US012564395B2

(12) United States Patent
Predick

(10) Patent No.: US 12,564,395 B2
(45) Date of Patent: Mar. 3, 2026

(54) MICRO RETRACTOR

(71) Applicant: Life Spine, Inc., Huntley, IL (US)

(72) Inventor: Daniel P. Predick, Wheat Ridge, CO (US)

(73) Assignee: Life Spine, Inc., Huntley, IL (US)

( * ) Notice: Subject to any disclaimer, the term of this patent is extended or adjusted under 35 U.S.C. 154(b) by 106 days.

(21) Appl. No.: 18/639,345

(22) Filed: Apr. 18, 2024

(65) Prior Publication Data

US 2024/0350130 A1 Oct. 24, 2024

Related U.S. Application Data

(60) Provisional application No. 63/460,456, filed on Apr. 19, 2023.

(51) Int. Cl.
*A61B 17/02* (2006.01)
*A61B 17/00* (2006.01)

(52) U.S. Cl.
CPC .............................. *A61B 17/0206* (2013.01); *A61B 2017/00367* (2013.01); *A61B 2017/00477* (2013.01)

(58) Field of Classification Search
CPC ............ A61B 17/0206; A61B 17/0293; A61B 17/3421; A61B 17/3439; A61B 17/02
See application file for complete search history.

(56) References Cited

U.S. PATENT DOCUMENTS

| | | | | | |
|---|---|---|---|---|---|
| 4,765,311 | A | * | 8/1988 | Kulik ................. | A61B 17/3417 600/222 |
| 6,224,545 | B1 | * | 5/2001 | Cocchia ............. | A61B 17/0206 600/233 |
| 6,520,967 | B1 | * | 2/2003 | Cauthen ............. | A61B 17/1757 606/86 R |
| 6,712,795 | B1 | * | 3/2004 | Cohen ................ | A61B 17/0206 604/233 |
| 8,262,569 | B2 | * | 9/2012 | Hestad ................... | A61B 17/02 600/219 |
| 9,131,935 | B2 | * | 9/2015 | Hamada ............. | A61B 17/0293 |
| 10,905,566 | B2 | * | 2/2021 | Shinbrot ............. | A61B 17/025 |
| 11,844,504 | B2 | * | 12/2023 | Sandham ............... | A61B 90/30 |

(Continued)

FOREIGN PATENT DOCUMENTS

| | | | | | |
|---|---|---|---|---|---|
| CN | 114469208 | A | * | 5/2022 | ............. A61B 90/30 |
| CN | 119385493 | A | * | 2/2025 | ......... A61B 17/0293 |
| EP | 3545857 | A3 | * | 1/2020 | ......... A61B 17/0293 |

*Primary Examiner* — Jacqueline T Johanas
(74) *Attorney, Agent, or Firm* — Bruce J. Bowman

(57) ABSTRACT

A micro retractor for tissue retraction during surgery has a head with an opening extending from an upper surface of the head to a lower surface of the head with a first leg fixed to a first side of the head opening and extending downward relative to the lower surface, and a second leg fixed to a member movable in the head opening and extending downward relative to the lower surface, together defining a channel allowing various medical instruments to be inserted therein during retraction. A distal first leg end and a distal second leg end meet, forming a pivot point wherein the dimension of the channel remains nearly fixed and tissue retraction at the pivot point remains constant, while the proximal second leg end is movable via the member to vary the dimension of the channel opening which also varies the dimension of the channel opening and the channel.

12 Claims, 5 Drawing Sheets

(56) References Cited

U.S. PATENT DOCUMENTS

| | | | | |
|---|---|---|---|---|
| 2003/0191371 | A1* | 10/2003 | Smith | A61B 17/02 |
| | | | | 600/210 |
| 2004/0082958 | A1* | 4/2004 | Michelson | A61F 2/4611 |
| | | | | 606/90 |
| 2004/0230191 | A1* | 11/2004 | Frey | A61B 17/0293 |
| | | | | 606/57 |
| 2005/0075643 | A1* | 4/2005 | Schwab | A61F 2/4611 |
| | | | | 606/90 |
| 2006/0089536 | A1* | 4/2006 | Perez-Cruet | A61B 17/3439 |
| | | | | 600/210 |
| 2006/0106416 | A1* | 5/2006 | Raymond | A61B 17/3439 |
| | | | | 606/198 |
| 2006/0217754 | A1* | 9/2006 | Boehm | A61B 17/025 |
| | | | | 606/191 |
| 2007/0027364 | A1* | 2/2007 | Schwer | A61B 17/0206 |
| | | | | 600/219 |
| 2007/0260125 | A1* | 11/2007 | Strauss | A61B 17/0293 |
| | | | | 600/219 |
| 2008/0077156 | A1* | 3/2008 | Emstad | A61B 17/025 |
| | | | | 606/90 |
| 2008/0132766 | A1* | 6/2008 | Dant | A61B 17/02 |
| | | | | 600/219 |
| 2009/0062619 | A1* | 3/2009 | Bjork | A61B 17/0206 |
| | | | | 600/219 |
| 2009/0275952 | A1* | 11/2009 | Lawson | A61B 17/025 |
| | | | | 606/90 |
| 2010/0076502 | A1* | 3/2010 | Guyer | A61B 17/34 |
| | | | | 600/184 |
| 2011/0034777 | A1* | 2/2011 | Ames | A61B 17/7077 |
| | | | | 600/206 |
| 2012/0029296 | A1* | 2/2012 | Mishra | A61B 17/3439 |
| | | | | 600/208 |
| 2012/0259177 | A1* | 10/2012 | Fiorella | A61B 90/57 |
| | | | | 600/228 |
| 2012/0310048 | A1* | 12/2012 | Siegal | A61B 17/0206 |
| | | | | 600/206 |
| 2013/0190558 | A1* | 7/2013 | Alexander | A61B 17/0293 |
| | | | | 600/37 |
| 2013/0289354 | A1* | 10/2013 | Ainsworth | A61B 1/32 |
| | | | | 606/246 |
| 2015/0257746 | A1* | 9/2015 | Seifert | A61B 17/3462 |
| | | | | 600/206 |
| 2017/0095241 | A1* | 4/2017 | Perler | A61B 90/30 |
| 2017/0333021 | A1* | 11/2017 | Heiges | A61B 17/3423 |
| 2019/0038273 | A1* | 2/2019 | Perler | A61B 17/02 |
| 2019/0254651 | A1* | 8/2019 | Coale | A61B 17/0206 |
| 2019/0298328 | A1* | 10/2019 | Popejoy | A61B 17/0206 |
| 2020/0245856 | A1* | 8/2020 | Berry | A61B 17/0293 |
| 2020/0323559 | A1* | 10/2020 | Skinner | A61B 17/3417 |
| 2021/0085307 | A1* | 3/2021 | Sandham | A61B 17/0293 |
| 2021/0298733 | A1* | 9/2021 | Tanaka | A61B 17/3423 |
| 2022/0387080 | A1* | 12/2022 | Hua | A61B 17/7032 |
| 2024/0350130 | A1* | 10/2024 | Predick | A61B 17/0206 |

* cited by examiner

MICRO RETRACTOR

CROSS-REFERENCE TO RELATED APPLICATIONS

This U.S. non-provisional patent application claims the benefit of and/or priority under 35 U.S.C. § 119(e) to U.S. provisional patent application Ser. No. 63/460,456 filed Apr. 19, 2023 titled "Micro Retractor," the entire contents of which is specifically incorporated herein by reference.

FIELD OF THE INVENTION

The present invention relates to medical instruments for surgical procedures and, more particularly, to medical retractors for surgical procedures.

BACKGROUND OF THE INVENTION

When performing a surgical procedure such as spine surgery, it is generally necessary to retract and hold open tissue at the incision site. This can be accomplished by using a medical instrument known as a retractor. One portion of the retractor is used to abut against tissue at one side of the incision while a second portion of the retractor is used to abut against an opposite side of the incision. The retractor is manipulated to move the first and second portions relative to one another in order to retract tissue. The retractor holds the retracted tissue in the retracted position. Once the tissue is retracted, internal surgical targets can be reached via various medical instruments.

As tissue is retracted, the incision gets wider at the retraction area. In many instances, this is desired. However, with minimally invasive surgery and micro invasive surgery that utilize cannulas and/or endoscopes, widening of the incision is not desirable. Such surgical procedures reduce the amount of tissue trauma by minimizing incision length and spread. This provides for better patient recovery.

It would therefore be desirable to have a medical instrument in the form of a retractor that minimizes the amount of tissue retraction of an incision while allowing various medical instruments to be introduced through the retracted incision and utilized. It would therefore be further desirable to have a medical instrument in the form of a retractor for minimally invasive and/or micro invasive surgical procedures that minimizes the amount of tissue retraction of an incision while allowing a cannula, endoscope, and/or other medical instrument to be introduced through the incision and utilized. Other desires are contemplated.

The present medical retractor addresses the above and more.

SUMMARY OF THE INVENTION

A medical instrument for retracting tissue during a surgical procedure particularly, but not necessarily, during spine surgery, has a channel defined by opposing legs for receiving a medical implement, the channel having a variably sizeable orifice to accommodate additional surgical implements, and whose opposing legs pivot at a distal end thereof, the distal end of the opposing legs having a dimension that remains relatively the same during expansion of the orifice.

The medical instrument in the form of a micro retractor, has a head with an opening extending from an upper surface of the head to a lower surface of the head and from a first side of the head opening to a second side of the head opening with a first leg fixed to the first side of the head opening and extending downward relative to the lower surface, and a second leg fixed to a member movably situated in the head opening and extending downward relative to the lower surface, the first and second legs opposing one another and together define a channel for allowing various medical implements to be inserted therein during retraction. The first leg defines a proximal first leg end and a distal first leg end. The second leg defines a proximal second leg end and a distal second leg end. The distal first leg end and the distal second leg end meet at a pivot area wherein the dimension of the pivot area remains relatively the same dimension as a channel opening orifice at the proximal first leg end and the proximal second leg end expands with movement of the proximal second leg end via the movable member, and tissue retraction at the pivot area remains relatively constant.

The member is manually movable within the head opening through a knob that is situated at the outside of the head and which has an externally threaded stem extending through a generally horizontal slot in the side wall of the head and into an internally threaded bore in a lateral side of the movable member. Rotation of the knob in one radial direction threads the externally threaded stem into the internally threaded bore of the member to tighten the knob against the side wall of the head to fix movement of the member. Rotation of the knob in an opposite radial direction unthreads the externally threaded stem out of the internally threaded bore of the member to loosen the knob relative to the side wall of the head to un-fix movement of the member and allow movement thereof.

The head of the micro retractor, in one form, is stadium shaped defining a first end and a second end opposite the first end. The opening of the head, in one form, is likewise stadium shaped. The head, and thus the generally horizontal is angled slightly downward to help hold the curvature of angulation of the second leg.

The first leg is defined by a first three-sided tube having a first leg end facing the first side of the head opening and a first open side opposite the first leg end. The second leg is defined by a second three-sided tube having a second leg end facing the second side of the head opening and a second open side opposite the second leg end. The second open side of the second three-sided tube is adjacent the first open side of the first three-sided tube, defining the variably dimensioned channel.

The distal end of the first three-sided tube may include one or more tangs that, in one aspect, serve as nerve root protection. The distal end of the second three-sided may also include one or more tangs that, in one aspect, serve as nerve root protection. The tangs may also aid in tissue retraction.

The present micro retractor is especially, but not necessarily, for vertebral disc preparation, spine implant installation or the like.

Further aspects of the present invention will become apparent from consideration of the drawings and the following description of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features will be better understood by reference to the accompanying drawings, wherein.

Figure 1:
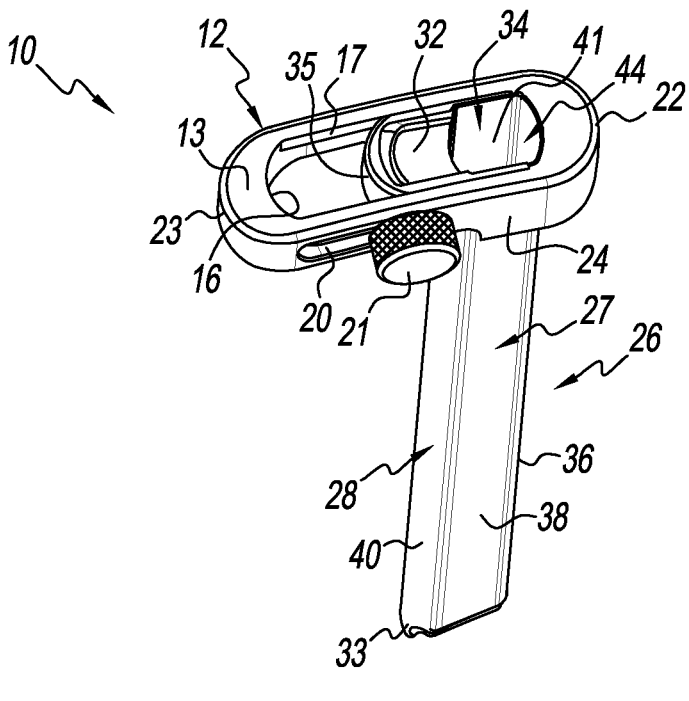
FIG. 1 is a top perspective view of the present micro retractor with the legs of the micro retractor shown in an initial un-retracted position.
Figure 2:
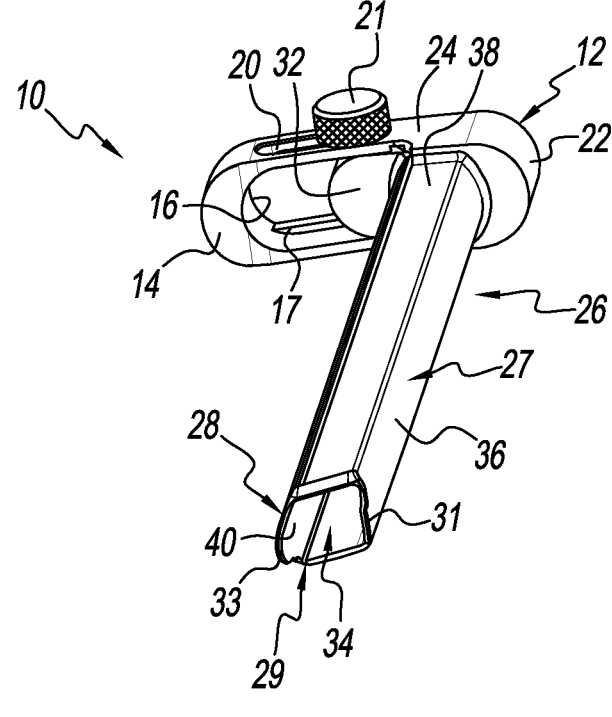
FIG. 2 is a bottom perspective view of the present micro retractor with the legs thereof in the un-retracted position.
Figures 3, 4:
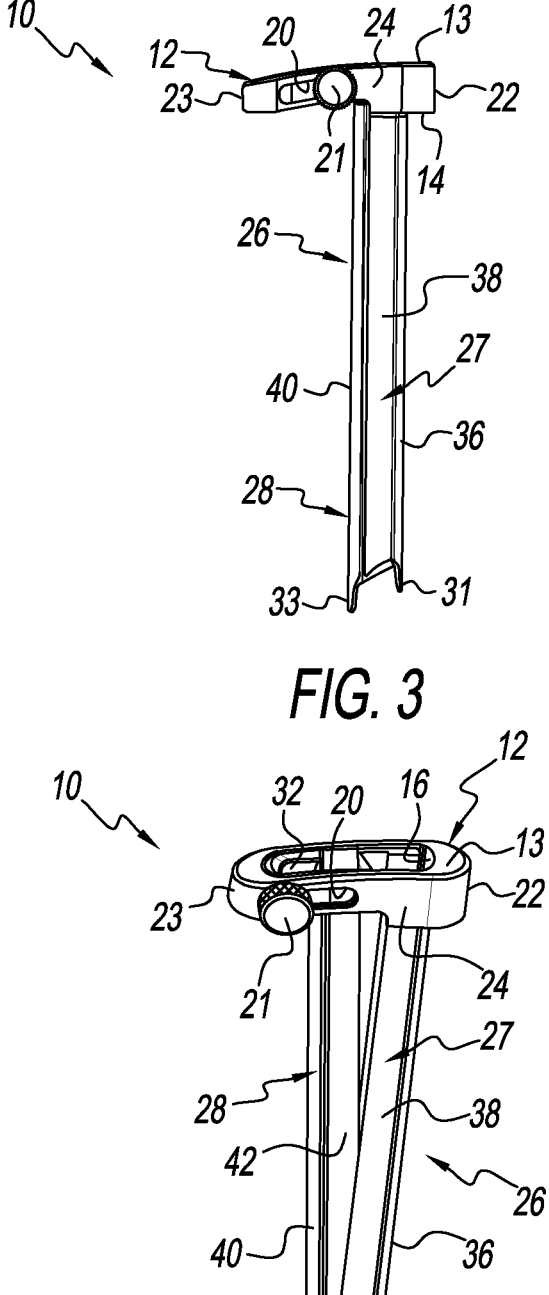
FIG. 3 is a side view of the present micro retractor with the legs thereof in the un-retracted position.
FIG. 4 is a side perspective view of the present micro retractor with the legs thereof in a retracted position.
Figure 5:
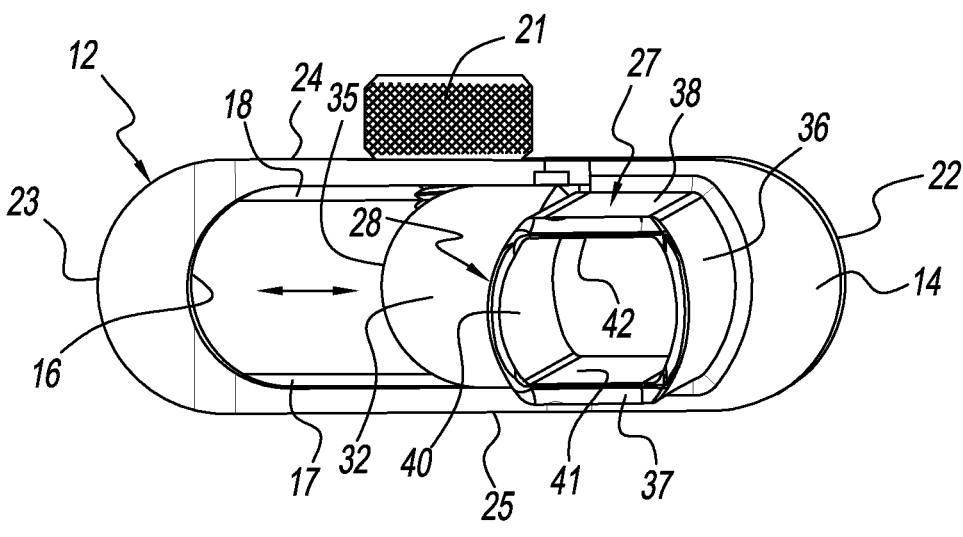
FIG. 5 is an enlarged bottom perspective view of the present micro retractor in the un-retracted position.

For the purposes of promoting an understanding of the principles of the invention reference will now be made to the embodiment illustrated in the drawings and specific language will be used to describe the same. It will nevertheless be understood that no limitation of the scope of the invention is thereby intended. Any alterations and further modifications in the described embodiment, and any further applications of the principles of the invention as described herein are contemplated as would normally occur to one skilled in the art to which the invention relates.

DETAILED DESCRIPTION OF THE INVENTION

Referring to FIGS. 1-10, there is shown a medical instrument, generally designated 10, in the form of a retractor and, more particularly, in the form of a micro retractor. The micro retractor 10 is made from one or more surgical grade materials. The micro retractor 10 has a head 12 having a stadium shape (elongated oval) defining an upper surface 13 and a lower surface 14. The head 12 has a opening 16 extending from the upper surface 13 to the lower surface 14 having a stadium shape (elongated oval) in similar fashion as the shape of head 12. The head 12 has a first end 22 that is arc-shaped and a second end 23 opposite the first end 22 that is likewise arc-shaped, the nomenclature first and second being arbitrary here and throughout unless specifically indicated otherwise. The head 12 also has a first linear lateral wall 24 extending between a first side of the first end 22 and a first side of the second end 23, and a second linear wall 25 opposite the first linear wall 24 between a second side of the first end 22 and a second side of the second end 23. The first linear wall 24 defines an outside facing away from the opening 16, and an inside facing the opening 16, with the inside of the first linear wall 24 having a first ledge, rail, track, or the like (collectively, first ledge) 18. The second linear wall 25 defines an outside facing away from the opening 16, and an inside facing the opening 16, with the inside of the second linear wall 25 having a second ledge, rail, track, or the like (collectively second ledge) 17.

A member 32 is situated in the opening 16 and is dimensioned to extend from the inside of the first linear wall 24 to the inside of the second linear wall 25. Particularly, a first lateral edge of the member 32 is configured to engage and travel along the first ledge 18 within the opening 16, while a second lateral edge of the member 32 is configured to engage and travel along the second ledge 17 within the opening 16. Movement or translation of the member 32 along the first and second ledges 18, 17 within the opening 16 as indicated by the two-headed arrow in the various figures is controlled manually via a knurled knob 21. A horizontal slot 20 is situated in the first linear wall 24 that extends from the outside of the first linear wall 24 to the inside of the first linear wall 24. The knurled knob 21 has an externally threaded stem (not seen) that extends through the horizontal slot 20 and into an internally threaded bore (not seen) in the side of the member 32.

Figure 6:
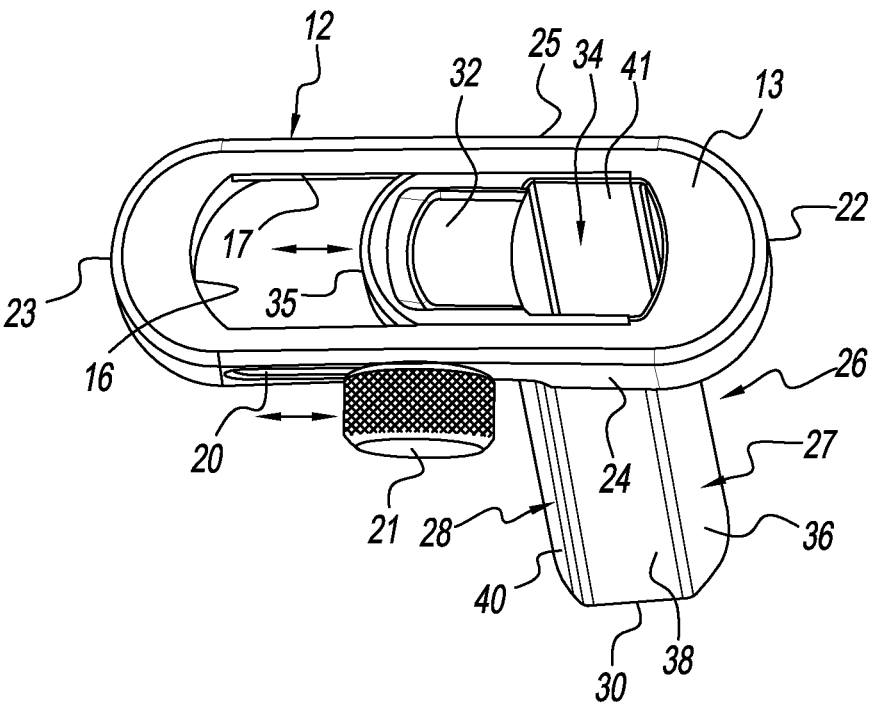
FIG. 6 is an enlarged top perspective view of the present micro retractor in the un-retracted position.

Translation of the member 32 along the first and second ledges 18, 17 and within the opening 16 is accomplished by manual movement of the knob 21 along the slot 20, as indicated by the double-headed arrow depicted in FIG. 6. Movement of the knob 21 along the slot 20 moves the attached threaded stem (not seen) which, in turn, moves (translates) the member 32 along and within the opening 16. Rotation of the knob 21 in one radial direction threads the threaded stem into the internally threaded bore (not seen) of the member 32 to tighten the knob 21 against the outside of the first linear wall 24 and relative to the slot 20 in order to fix position of the member 32 in the opening 16. Rotation of the knob 21 in the opposite radial direction unthreads the threaded stem from the internally threaded bore (not seen) of the member 32 to loosen the knob 21 from against the outside of the first linear wall 24 and relative to the slot 20 in order to allow translation of the member 32 in the opening 16. In this manner, the member 32 may be positioned accordingly and then held in place.

Figure 7:
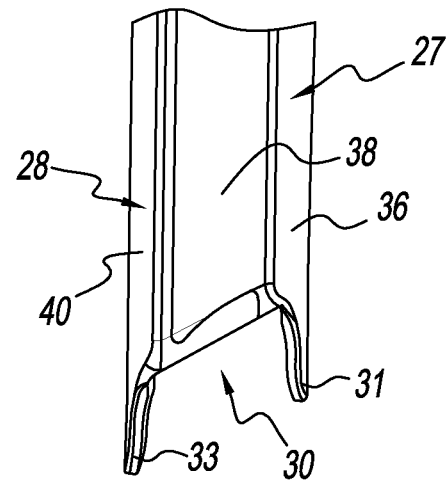
FIG. 7 is an enlarged perspective partial view of the legs of the present micro retractor in the un-retracted position.

The micro retractor 10 further has a spreader 26 defined by a first leg 27 and a second leg 28. The first leg 27 is stationary relative to the opening 16 and is defined by a rear wall 36, a first side wall 37, and a second side wall 38. The first side wall 37 is transverse to a first side of the first rear wall 36, while the second side wall 38 is transverse to a second side of the rear wall 36. The first or stationary leg 27 is thus open along its length opposite the first rear wall 36. The proximal ends of the rear wall 36, the first side wall 37, and the second side wall 38 are fixed to and extend from an end of the opening 16 directly opposite the first end 22. As best seen in FIG. 7, the distal end of the rear wall 36 has a first tang, flange, projection, or the like (collectively, tang) 31 that provides nerve root protection and/or retraction. The distal end of the rear wall 36 may have more than one tang or no tang. The first leg 27 is thus defined by a three-sided, generally rectangular tube with an open side opposite the rear wall 36, the open side facing the second end 23 of the head 12.

The second leg 28 articulates and is defined by a rear wall 40, a first side wall 41, and a second side wall 42. The first side wall 41 is transverse to a first side of the rear wall 40, while the second side wall 42 is transverse to a second side of the rear wall 40. The second leg 28 is thus open along its length opposite the rear wall 40. The proximal ends of the rear wall 40, the first side wall 41, and the second side wall 42 are fixed to and extend from the member 32. As best seen in FIG. 7, the distal end of the rear wall 40 has a second tang, flange, projection, or the like (collectively, tang) 33 that provides nerve root protection and/or retraction. The distal end of the rear wall 40 may have more than one tang or no tang. The second leg 28 is thus defined by a three-sided, generally rectangular tube with an open side opposite the rear wall 40, the open side facing the first end 22 of the head 12 and adjacent to the open side of the first leg 27. The second leg 28 nests in the first leg 27. Because of the position of the open sides of the first and second legs 27, 28, the first and second legs 27, 28 together define a channel 34 bounded by the rear and side walls of the first and second legs, and which extends from the opening 16 (proximal ends of the first and second legs 27, 28) to the distal ends of the first and second legs 27, 28. The channel 34 defines a distal opening or egress 29 (see FIG. 2) and a proximal opening 44 (see FIG. 1).

Because the proximal end of the second leg 28 is connected to the movable member 32, the proximal end of the second leg 28 moves with the member 32. As the member 32 moves towards the second end 23, the proximal opening 44, as well as the channel 34, widens. However, while the proximal opening widens, the distal end of the first and second legs 27, 28 pivots at a pivot/pivot location 30 (see FIG. 4) where the distal ends of the first and second ends meet such that the size of the distal opening/egress 29 (tip) remains nearly unchanged to alleviate and/or ensure there is no additional stress put on nerve roots at the incision/retraction site. There is some minimal movement of the tip, with the goal being as minimal as possible.

Figure 10:
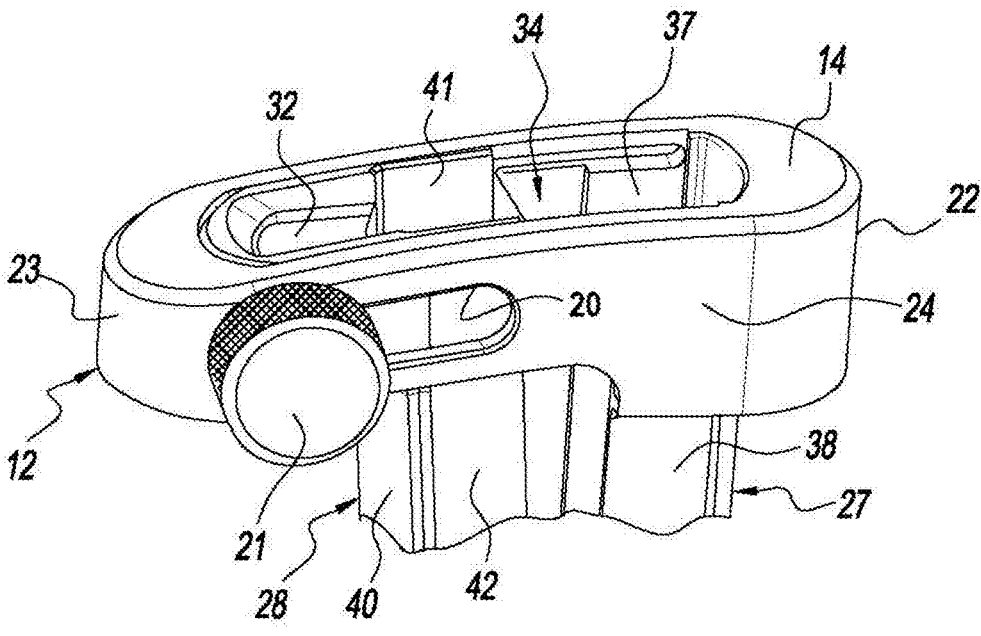
FIG. 10 is an enlarged side perspective partial view of the head of the present micro retractor in a retracted position.

As best seen in FIG. 10, the head 12, including the upper surface 14 is curved slightly downward from the first (rear) end 22 to the second (front) end 23. As such, the slot 20 therefore also curves slightly downward between the first end 22 and the second end 23. Such curvature helps hold the curvature of angulation of the second leg 28 as it pivots relative to the first leg 27.

Figure 8:
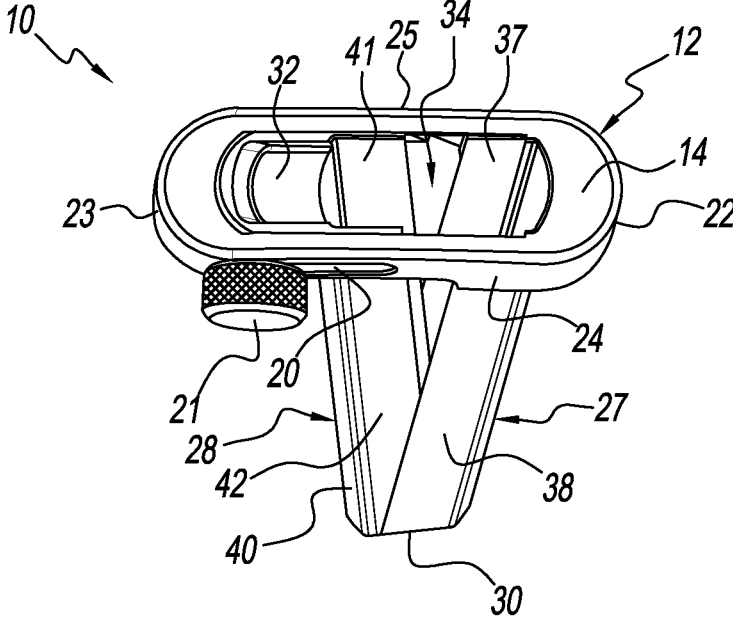
FIG. 8 is a top perspective view of the present micro retractor with the legs thereof in a retracted position.

When the first and second legs 27, 28 are in a fully un-retracted position as depicted in FIGS. 1-3 and 5-7, the channel 34 is dimensioned to receive an endoscope (not shown) or other medical instrument. As the member 32 is moved along the first and second ledges 18, 17 within the opening 16 from the un-retracted position, the second leg 28 pivots about the pivot location 30 whereby the dimension of the channel 34 widens above the pivot location 30 (see, e.g., FIGS. 4, 8 and 10). The amount of widening depends on the position of the member 32. FIGS. 4, 8 and 10, for example, depict the micro retractor 10 in a fully retracted position wherein the member 32 has been moved fully forward (towards the front end 23). This position provides the widest channel 34 and thus accommodation for the greatest number of medical instruments that can be received the channel 34. While not shown, the micro retractor 10 can be set in intermediate retraction positions that are between the fully un-retracted position and the fully retracted position.

Figure 9:
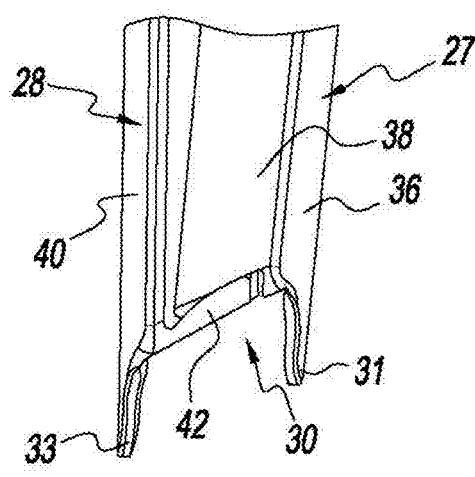
FIG. 9 is an enlarged perspective view of the legs of the present micro retractor in the retracted position of FIG. 8.

FIG. 7 shows the pivot location 30 at the distal ends of the first and second legs 27, 28 when the micro retractor 10 is in an un-retracted position. In the un-retracted position, the pivot location 30 has a dimension defined by the dimension of the distal ends of the first and second legs 27, 28 and the first and second tangs 31, 33. FIG. 9 shows the pivot location 30 at the distal ends of the first and second legs 27, 28 when the micro retractor 10 is in a retracted position. In the retracted position, the pivot location dimension remains relatively unchanged (nearly fixed).

The micro retractor 10 is inserted into an incision in the un-retracted position. The channel 34 accommodates an endoscope (not shown) or other medical instrument (not shown). When needed, the channel 34 aperture at the opening 16 of the head 12, can be widened by moving the member 32 via the knob 21. The position of the member 32 within the opening 16, and thus the proximal end of the second leg 28, determines the size of the channel 34 aperture. When in a retracted position, the channel 34 accommodates more than one medical instrument.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention.

What is claimed is:

1. A medical instrument for retracting tissue during a surgical procedure comprising:

a head having an upper surface, a lower surface, and an opening extending from the upper surface to the lower surface, the opening defining an opening wall with a first opening end, and a second opening end opposite the first opening end;

a moving member situated in the opening and connected to the opening wall for translation within the opening;

an adjustor situated in the head and attached to the moving member for controlling position of the moving member within the opening;

a first leg defining a proximal first leg end and a distal first leg end, the proximal first leg end disposed at the first opening end and extending from the lower surface of the head; and a second leg defining a proximal second leg end and a distal second leg end, the proximal second leg end connected to and extending from the moving member;

the distal first leg end and the distal second leg end defining a pivot point; and the first and second legs defining a channel having a variably-sizable channel opening controlled in size by position of the moving member in the opening of the head, and a channel egress at the pivot point, the channel extending from the variably-sizable channel opening to the channel egress;

wherein the first leg is characterized by a first three-sided tube defining a first open side; and the second leg is characterized by a second three-sided tube defining a second open side;

the first and second legs are oriented such that the first open side of the first leg faces the second open side of the second leg.

2. The medical instrument of claim 1, wherein:

the first three-sided tube is further characterized by a first back side opposite the first open side, a first lateral side transverse to the first back side, and a second lateral side transverse to the first back side and opposite the first lateral side of the first three-sided tube; and the second three-sided tube is further characterized by a second back side opposite the second open side, a third lateral side transverse to the second back side, and a fourth lateral side transverse to the second back side and opposite the third lateral side.

3. The medical instrument of claim 2, wherein:

the first back side has a first tang at a first distal end of the first back side; and the second back side has a second tang at a first distal end of the second back side.

4. The medical instrument of claim 2, wherein:

the head further defines an outer surface;

the medical instrument further comprises a horizontal slot in the head extending from the outer surface of the head to the opening wall; and the adjuster comprises a knob radially outward of the outer surface of the head and having a stem situated in and extending through the slot, and connected to the moving member for manual manipulation of the moving member via the knob.

5. The medical instrument of claim 4, wherein the adjuster allows for temporary fixation of the moving member in the opening.

6. The medical instrument of claim 5, wherein the head is angled downward.

7. The medical instrument of claim 5, wherein the horizontal slot is angled downward.

8. The medical instrument of claim 4, wherein the adjuster further comprises an internally threaded bore in the moving member, and the stem is externally threaded.

9. A retractor for retracting tissue during a surgical procedure comprising:

a stadium shaped head having an upper surface, a lower surface, and a stadium shaped opening extending from the upper surface to the lower surface, the stadium shaped opening defining a stadium shaped opening wall with a first opening end, and a second opening end opposite the first opening end;

a moving member situated in the stadium shaped opening and connected to the stadium shaped opening wall for translation within the stadium shaped opening;

an adjustor situated in the stadium shaped head and attached to the moving member for controlling position of the moving member within the stadium shaped opening;

a first leg defining a proximal first leg end and a distal first leg end, the proximal first leg end disposed at the first opening end and extending from the lower surface of the head; and a second leg defining a proximal second leg end and a distal second leg end, the proximal second leg end connected to and extending from the moving member;

the distal first leg end and the distal second leg end defining a pivot point; and the first and second legs defining a channel having a variably-sizable channel opening controlled in size by position of the moving member in the stadium shaped opening of the stadium shaped head, and a nearly fixed size fixed-size channel egress at the pivot point, the channel extending from the variably-sized channel opening to the nearly fixed-size channel egress;

wherein the first leg is characterized by a first three-sided tube defining a first open side; and the second leg is characterized by a second three-sided tube defining a second open side;

the first and second legs are oriented such that the first open side of the first leg faces the second open side of the second leg.

10. The retractor of claim 9 wherein:

the first three-sided tube is further characterized by a first back side opposite the first open side, a first lateral side transverse to the first back side, and a second lateral side transverse to the first back side and opposite the first lateral side of the first three-sided tube; and the second three-sided tube is further characterized by a second back side opposite the second open side, a third lateral side transverse to the second back side, and a fourth lateral side transverse to the second back side and opposite the third lateral side.

11. The retractor of claim 10, wherein:

the first back side has a first tang at a first distal end of the first back side; and the second back side has a second tang at a first distal end of the second back side.

12. The retractor of claim 11, wherein:

the stadium shaped head further defines a stadium shaped outer surface;

the retractor further comprises a horizontal slot in the stadium shaped head extending from the outer surface of the stadium shaped head to the stadium shaped opening wall; and the adjuster comprises a knob radially outward of the outer surface of the stadium shaped head and having a stem situated in and extending through the horizontal slot, and connected to the moving member for manual manipulation of the moving member via the knob.

* * * * *